(12) United States Patent
Mongrenier

(10) Patent No.: US 10,987,276 B2
(45) Date of Patent: *Apr. 27, 2021

(54) DEVICE FOR STORING ELEMENTS

(71) Applicant: BIOLOG-ID, Paris (FR)

(72) Inventor: Jean-Claude Mongrenier, Versailles (FR)

(73) Assignee: BIOLOG-ID, Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/338,839

(22) PCT Filed: Oct. 24, 2016

(86) PCT No.: PCT/EP2016/075498
§ 371 (c)(1),
(2) Date: Apr. 2, 2019

(87) PCT Pub. No.: WO2018/065075
PCT Pub. Date: Apr. 12, 2018

(65) Prior Publication Data
US 2019/0247276 A1    Aug. 15, 2019

(30) Foreign Application Priority Data
Oct. 3, 2016 (FR) ...................... 1659518

(51) Int. Cl.
*A61J 1/10* (2006.01)
*A61M 1/02* (2006.01)
(Continued)

(52) U.S. Cl.
CPC ................ *A61J 1/10* (2013.01); *A61M 1/025* (2013.01); *A61M 1/0277* (2014.02);
(Continued)

(58) Field of Classification Search
CPC .......... G06K 7/10366; G06K 7/10415; G06K 7/10356; A61G 12/001; A61M 1/0286;
(Continued)

(56) References Cited

U.S. PATENT DOCUMENTS 3,722,964 A   3/1973   Chitester et al.
4,114,559 A   9/1978   Rogen
(Continued)

FOREIGN PATENT DOCUMENTS

AT        403245 B      12/1997
AU    2017236045 B2      3/2020
(Continued)

OTHER PUBLICATIONS

French Search Report for Application No. 1659518, dated Jan. 5, 2017.
(Continued)

*Primary Examiner* — Suezu Ellis
(74) *Attorney, Agent, or Firm* — Nixon & Vanderhye

(57) ABSTRACT

A device is provided for storing elements, each element including a first wireless communication unit. The device includes at least two drawer units each including: a drawer including a bottom defining at least one location for receiving an element; for each location, at least one second wireless communication unit including an antenna having a radiation-zone field, each antenna having a first state in which the antenna is activated and a second state in which the antenna is deactivated; and a data-processing unit able to control the activation and deactivation of the antenna of each second communication unit according to a control law.

11 Claims, 4 Drawing Sheets

(51) Int. Cl.
  *G06K 7/10* (2006.01)
  *B65G 1/00* (2006.01)
  *B65G 1/02* (2006.01)

(52) U.S. Cl.
  CPC ............ *A61M 1/0286* (2014.02); *B65G 1/00* (2013.01); *B65G 1/02* (2013.01); *G06K 7/10415* (2013.01); *A61J 2205/60* (2013.01); *B65G 2203/046* (2013.01)

(58) Field of Classification Search
  CPC ..... A61M 1/0245; A61M 1/025; G07F 11/62; G07F 17/0092; G06F 19/3462; G16H 20/13; G06Q 10/087; G06Q 10/0875; A61J 7/0084; A61J 2205/60; B65G 1/00; B65G 1/02; B65G 2203/046
  USPC .................................................. 235/492, 385
  See application file for complete search history.

(56) References Cited

U.S. PATENT DOCUMENTS

| | | | |
|---|---|---|---|
| 4,608,178 A | 8/1986 | Johansson | |
| 4,688,026 A | 8/1987 | Scribner | |
| 4,857,716 A | 8/1989 | Gombrich | |
| 4,871,439 A | 10/1989 | Enzer | |
| 4,952,913 A | 8/1990 | Pauley | |
| 5,100,564 A | 3/1992 | Pall | |
| 5,263,929 A | 11/1993 | Falcone | |
| 5,300,060 A | 4/1994 | Nelson | |
| 5,507,525 A | 4/1996 | Leuenberger | |
| 5,527,472 A | 6/1996 | Bellotti | |
| 5,572,873 A | 11/1996 | Lavigne | |
| 5,618,662 A | 4/1997 | Lin | |
| 5,635,917 A | 6/1997 | Todman | |
| 5,674,741 A | 10/1997 | Watanabe | |
| 5,709,472 A | 1/1998 | Prusik | |
| 5,769,811 A | 6/1998 | Stacey | |
| 5,839,806 A | 11/1998 | Liu | |
| 5,852,590 A | 12/1998 | De La Huerga | |
| 5,936,527 A | 8/1999 | Isaacman | |
| 5,969,606 A | 10/1999 | Reber | |
| 5,980,501 A | 11/1999 | Gray | |
| 6,032,155 A | 2/2000 | De La Huerga | |
| 6,036,101 A | 3/2000 | Hass | |
| 6,113,554 A | 9/2000 | Gilcher | |
| 6,122,704 A | 9/2000 | Hass | |
| 6,285,285 B1 | 9/2001 | Mongrenier | |
| 6,294,997 B1 | 9/2001 | Paratore | |
| 6,382,416 B1 | 5/2002 | Gainey | |
| 6,613,554 B2 | 9/2003 | Wei | |
| 6,712,276 B1 | 3/2004 | Abali | |
| 8,342,400 B1* | 1/2013 | Reese | G06F 19/3462 235/385 |
| 8,770,479 B1 | 7/2014 | Shoenfeld | |
| 9,275,262 B2 | 3/2016 | Mongrenier | |
| 2001/0006368 A1 | 7/2001 | Maloney | |
| 2001/0033233 A1 | 10/2001 | Jentsch | |
| 2001/0034614 A1 | 10/2001 | Fletcher-Haynes | |
| 2002/0013523 A1 | 1/2002 | Csore | |
| 2002/0023441 A1 | 2/2002 | Bara | |
| 2002/0143320 A1 | 10/2002 | Levin | |
| 2002/0183882 A1 | 12/2002 | Dearing | |
| 2002/0186145 A1 | 12/2002 | Chainer | |
| 2003/0072676 A1 | 4/2003 | Fletcher-Haynes | |
| 2003/0099158 A1 | 5/2003 | De La Huerga | |
| 2003/0132298 A1 | 7/2003 | Swartz | |
| 2004/0044326 A1 | 3/2004 | Kranz | |
| 2004/0046020 A1* | 3/2004 | Andreasson | A61J 1/14 235/385 |
| 2004/0100380 A1 | 5/2004 | Lindsay | |
| 2004/0151633 A1 | 8/2004 | De Gaulle | |
| 2004/0166583 A1 | 8/2004 | De Gaulle | |
| 2004/0212507 A1 | 10/2004 | Zweig | |
| 2005/0091896 A1 | 5/2005 | Kotik | |
| 2005/0127090 A1 | 6/2005 | Sayers | |
| 2005/0276728 A1 | 12/2005 | Muller-Cohn | |
| 2005/0285715 A1 | 12/2005 | Comunale | |
| 2007/0018819 A1 | 1/2007 | Streeb | |
| 2007/0023513 A1 | 2/2007 | Andreasson et al. | |
| 2007/0123809 A1 | 5/2007 | Weiss | |
| 2007/0220796 A1 | 9/2007 | Riley | |
| 2007/0272746 A1 | 11/2007 | Ortiz | |
| 2008/0104993 A1 | 5/2008 | Zenobi | |
| 2008/0203160 A1 | 8/2008 | Lee | |
| 2008/0208750 A1 | 8/2008 | Chen | |
| 2008/0264962 A1* | 10/2008 | Schifman | G07F 11/62 221/1 |
| 2008/0283596 A1 | 11/2008 | Ishida | |
| 2008/0316045 A1* | 12/2008 | Sriharto | G06Q 50/22 340/10.1 |
| 2009/0134997 A1 | 5/2009 | Godlewski | |
| 2009/0189816 A1 | 7/2009 | Nikitin | |
| 2009/0251293 A1* | 10/2009 | Azevedo | G07G 1/009 340/10.1 |
| 2010/0206948 A1 | 8/2010 | Seremjian | |
| 2011/0140831 A1 | 6/2011 | Michael | |
| 2011/0320322 A1 | 12/2011 | Roslak | |
| 2012/0044054 A1 | 2/2012 | Hussain | |
| 2015/0015373 A1 | 1/2015 | Mongrenier | |
| 2016/0042313 A1 | 2/2016 | Caputo et al. | |
| 2016/0113721 A1* | 4/2016 | Seremjian | H04B 5/0062 340/12.51 |
| 2017/0177832 A1* | 6/2017 | Caputo | G06F 19/30 |
| 2017/0196128 A1* | 7/2017 | Elizondo, II | G06F 1/182 |
| 2019/0220638 A1* | 7/2019 | Mongrenier | G07G 1/009 |
| 2019/0307936 A1* | 10/2019 | Rushing | B01F 15/065 |

FOREIGN PATENT DOCUMENTS

| | | |
|---|---|---|
| CA | 2307517 A1 | 10/2000 |
| CA | 2545978 A1 | 11/2007 |
| CA | 2572649 C | 1/2017 |
| CN | 2280671 Y | 5/1998 |
| EP | 0733377 A2 | 9/1996 |
| EP | 0598624 B1 | 9/1998 |
| EP | 0 639 384 B1 | 2/2002 |
| EP | 1 262 161 A1 | 12/2002 |
| EP | 1 526 484 A2 | 4/2005 |
| EP | 1 693 807 A1 | 8/2006 |
| EP | 2 186 480 B1 | 5/2014 |
| EP | 3 076 339 A1 | 10/2016 |
| FR | 2581044 A1 | 10/1986 |
| FR | 2 777 378 A1 | 10/1999 |
| FR | 2 787 220 A1 | 6/2000 |
| FR | 2 791 795 A1 | 10/2000 |
| FR | 2 796 182 A1 | 1/2001 |
| FR | 2 825 637 A1 | 12/2002 |
| FR | 2 825 638 A1 | 12/2002 |
| FR | 2 827 176 A1 | 1/2003 |
| FR | 2985590 A1 | 7/2013 |
| FR | 2988936 A1 | 10/2013 |
| FR | 3 047 185 A1 | 8/2017 |
| FR | 3 053 498 A1 | 1/2018 |
| JP | H10-212028 A | 8/1998 |
| JP | 2004-537352 A | 12/2004 |
| JP | 2005-503870 A | 2/2005 |
| JP | 2007-525383 A | 9/2007 |
| JP | 2008-540063 A | 11/2008 |
| JP | 2009-083954 A | 4/2009 |
| JP | 2013-519177 A | 5/2013 |
| JP | 2014-513225 A | 5/2014 |
| WO | 94/01193 A1 | 1/1994 |
| WO | 96/14043 A1 | 5/1996 |
| WO | 99/04837 A1 | 2/1999 |
| WO | 99/25397 A2 | 5/1999 |
| WO | 99/53467 A1 | 10/1999 |
| WO | 99/56696 A1 | 11/1999 |
| WO | 00/42969 A1 | 7/2000 |
| WO | 00/45331 A1 | 8/2000 |
| WO | 02/07800 A1 | 1/2002 |
| WO | 02/38101 A2 | 5/2002 |
| WO | 03/026724 A1 | 4/2003 |

(56) References Cited

FOREIGN PATENT DOCUMENTS

| WO | 2006/035465 A1 | 4/2006 |
|---|---|---|
| WO | 2009/043084 A1 | 4/2009 |
| WO | 2010/004331 A1 | 1/2010 |
| WO | 2011/100356 A1 | 8/2011 |
| WO | 2012/142314 A1 | 10/2012 |
| WO | 2016/065113 A1 | 4/2016 |

OTHER PUBLICATIONS

International Preliminary Report on Patentability for Application No. PCT/EP2016/075498, dated Aug. 16, 2017.
International Search Report for Application No. PCT/EP2016/075498, dated Apr. 19, 2017.
Amador et al., "Application of RFID Technologies in the Temperature Mapping of the Pineapple Supply Chain," Sensing and Instrumentation for Food and Quality and Safety, Mar. 2009, 3:26-33.
Borghino, Dario, "Intelligent blood bags optimize supplies and prevent dangerous mistakes," Dec. 14, 2009, https://newatlas.com/intelligent-blood-bags/13583/.
Gibson et al., "The Effect of Varying Temperatures on the Post-Transfusion Survival of Whole Blood During Depot Storage and After Transportation by Land and Air," Storage Temperature and Red Cell Preservation, Aug. 31, 1946, pp. 747-755.
Hamil, T.R., "The 30-minute rule for reissuing blood: are we needlessly discarding units?" Transfusion, 1990; 30:58-62.
Intelligent blood bags (Dec. 1, 2009) retrieved Dec. 17, 2018 from https://phys.org/news/2009-12-intelligent-blood-bags.html.
Kim et al., "Smart Blood Bag Management System in a Hospital Environment," PWC 2006, Computer Science, vol. 4217.
Pick et al., "Temperature Changes in Donor Blood under Different Storage Conditions," Transfusion, vol. 11, No. 4, Jul.-Aug. 1971 pp. 213-215.
Saxena et al., "The Risk of Bacterial Growth in Units of Blood that Have Warmed to More Than 10° C.," Brief Scientific Reports, vol. 94, No. 1, pp. 80-83.
Saxena et al., "A comprehensive assessment program to improve blood-administering practices using the FOCUS-PDCA model," Transfusion, vol. 44, Sep. 2004, pp. 1350-1356.
Shields, C.E., "Studies on Stored Whole Blood, Effects of Temperature and Mechanical Agitation on Blood with and without Plasma," vol. 10, No. 4, Jul.-Aug. 1970, pp. 155-162.
"Blood bags with RFIP chips: Secure transport from vein to vein," Jun. 15, 2010, Reference No. PN201005.
Shulman et al., "Assessing Blood Administering Practices," Arch Pathol Lab Med, vol. 123, Jul. 1999, pp. 595-598.

\* cited by examiner

DEVICE FOR STORING ELEMENTS

BACKGROUND OF THE INVENTION

Field of the Invention

The present invention relates to a device for storing elements.

The present invention also relates to an installation comprising such a storage device.

Description of the Related Art

The elements are, for example, pouches containing biological products, such as blood products (pouches of primary blood, plasma, platelets, red blood cells . . . ) or cellular engineering products (cells, strains, etc.), or pouches for of drugs, such as chemotherapy pouches.

It is known to store such pouches in cooling structures formed by drawers in which the pouches are inserted. The pouches inserted in such structures generally comprise an identifying tag, such as an RFID (radio frequency identification) tag, in which information relating to the corresponding pouch is stored. In addition, a reader, such as an RFID reader, is arranged in relation to the intended location of the pouches of each drawer in order to read and update the information contained in the tags of the pouches.

However, when the tags of the pouches are not positioned directly opposite the reader in the drawer, the reading of the information contained in the tag of the pouches may not be carried out.

There is therefore a need for a device for storing elements allowing the reliable checking of the state of the elements without encumbering the storage space.

BRIEF SUMMARY OF THE INVENTION

For this purpose, the object of the invention is a device for storing elements, wherein each element comprises a first wireless communication unit, and wherein the device comprises at least one drawer assembly, and each drawer assembly comprises:
  a support comprising a housing,
  a drawer positioned in the housing of the support and slidable relative to the support, wherein the drawer comprises a bottom defining at least one slot for receiving an element,
  for each slot, at least one second wireless communication unit capable of transmitting radio frequency waves, wherein the second communication unit is designed to communicate with all the first communication units,
  wherein the bottom of the drawer is made of a material that may be traversed by radio frequency waves transmitted by the, or each, second communication unit, wherein the, or each, second communication unit is arranged below the bottom of the drawer in relation to the corresponding slot of the bottom of the drawer, in order to allow communication between the second communication unit and the first communication unit of an element received in the slot.

According to particular embodiments, the device comprises one or more of the following characteristics, taken separately or in any technically feasible combination:
  the bottom of the drawer is made of plastic;
  the elements are containers of biological products, medicines or therapeutic preparations;
  each first communication unit is a radio identification tag and each second communication unit is a radio identification reader;
  each second communication unit is secured to the support of the corresponding drawer assembly; while each second communication unit is secured to the drawer of the corresponding drawer assembly;
  the device comprises a plurality of drawer assemblies, wherein an upper end and/or a lower end of the support of each drawer assembly comprises an assembly member with a respective complementary assembly member, of a lower end or of a upper end of the support of another of the drawer assemblies, so that the drawer assemblies are assembled on top of one another to form a vertical stack;
  each first communication unit comprises information relative to the element corresponding to said first communication unit, each second communication unit being, if appropriate, able to communicate with the first communication unit of the element received in the slot facing said second communication unit for obtaining information relative to the element, wherein the device further comprises a processing unit connected to each second communication unit, and wherein the processing unit is able to determine from the communicated information, the occupation of each slot and, where appropriate, the state of the element received in the slot, wherein the processing unit is able to trigger an alarm according to the occupation of each slot and, if applicable, determine the state of the element corresponding to the slot.

The invention also relates to an installation comprising:
  an enclosure comprising an internal compartment, and
  a device according to the first aspect of the invention, wherein the device is arranged in the inner compartment of the enclosure.

According to particular embodiments, the device comprises one or more of the following characteristics, taken separately or in any technically feasible combination:
  the enclosure is a refrigerating enclosure;
  the elements are platelet containers, while the enclosure is a platelet stirrer.

BRIEF DESCRIPTION OF THE DRAWINGS

Other features and advantages of the invention will become apparent upon reading the following description of embodiments of the invention, given by way of example only and with reference to the drawings, wherein.

DETAILED DESCRIPTION OF THE PREFERRED EMBODIMENTS

Figure 1:
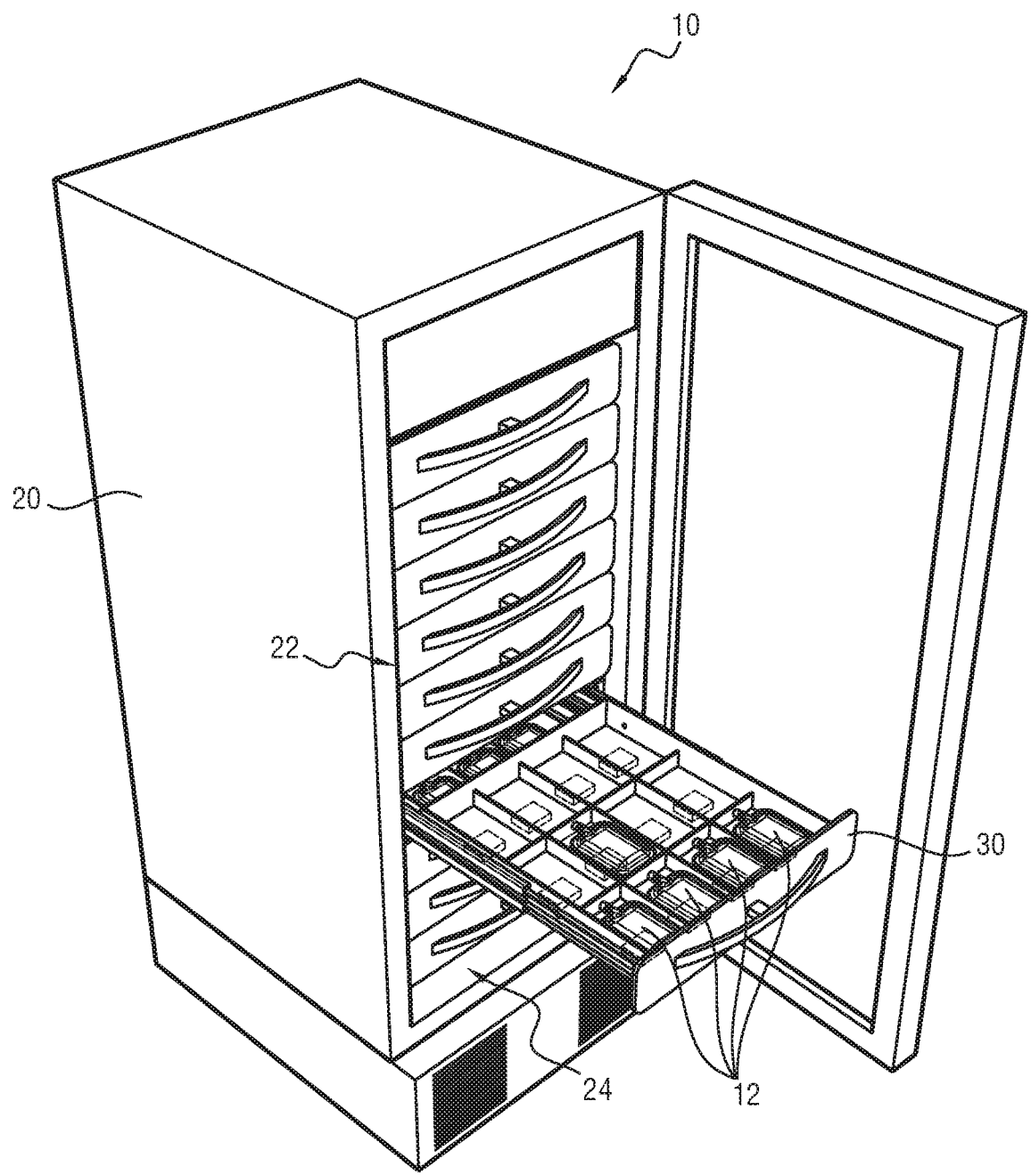
FIG. 1 shows a schematic representation in perspective of an installation comprising a storage device.

An element storage 12 installation 10 is illustrated in FIG. 1.

Figure 2:
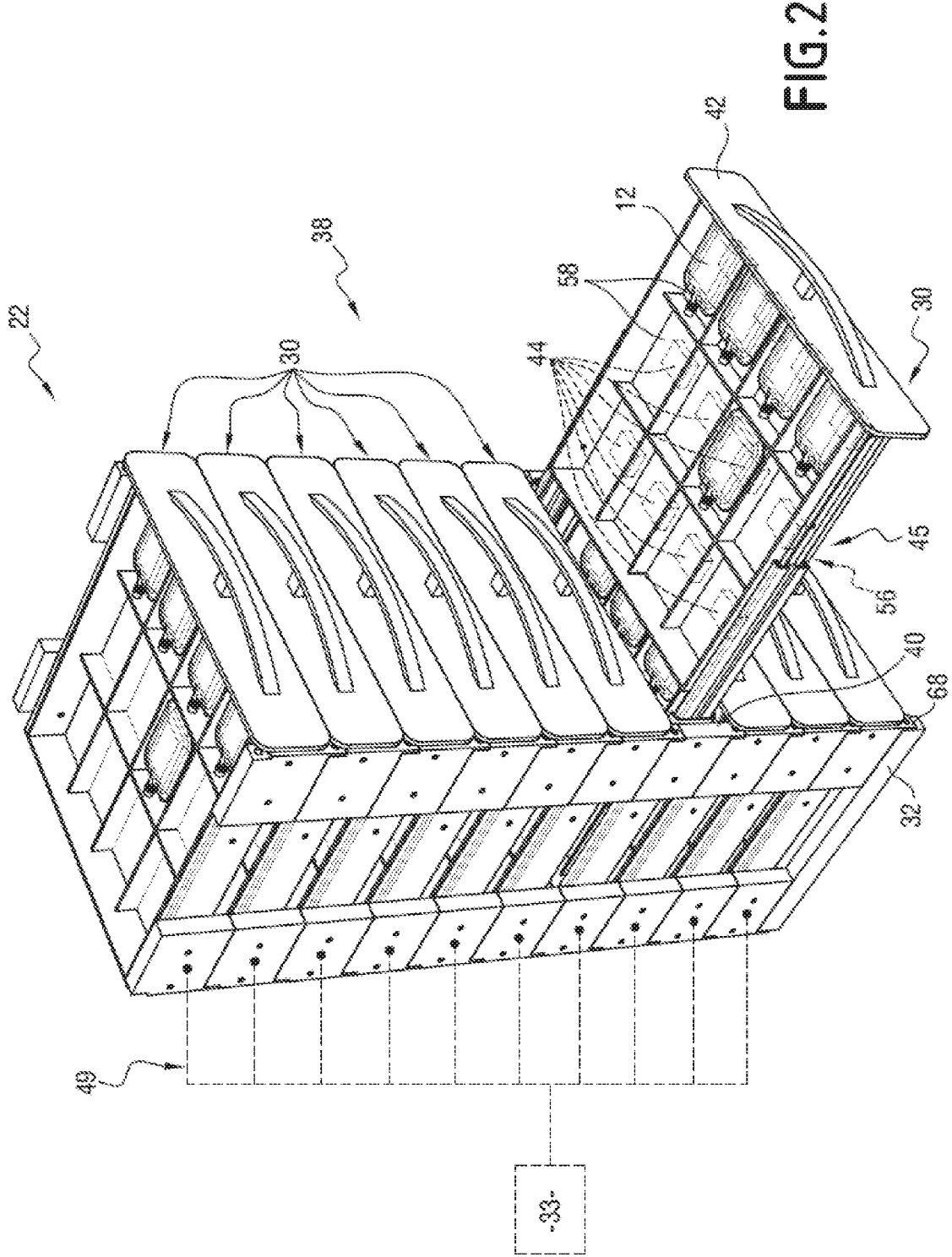
FIG. 2 shows a schematic representation in perspective of the storage device of FIG. 1.

The elements 12 are, for example, containers (visible in FIG. 2). In general, a container designates any type of pouch that is intended to contain products, the use of which is conditioned by strict storage constraints.

More particularly, the elements 12 are, for example, pouches containing biological products such as blood products (pouches for primary blood, plasma, platelets, red blood cells, etc.) or cellular engineering products (human cells or animal, especially human or animal stem cells, products derived from human or animal cells).

Alternatively, the elements 12 are pouches for drugs or therapeutic preparations containing one or more active ingredients or drugs, such as chemotherapy pouches that generally contain a solute and one or more chemotherapy active ingredients.

More generally, the elements 12 are able to contain any product intended to perfuse a human or an animal.

Figure 4:
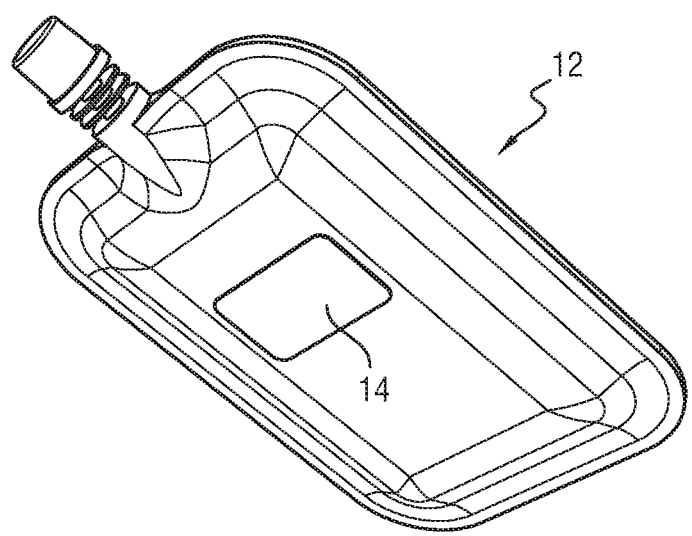
FIG. 4 shows a schematic representation of an element intended to be stored in the device of FIG. 1.

As may be seen in FIG. 4, each element 12 comprises a first wireless communication unit 14. Each first communication unit 14 is, for example, a tag, such as an adhesive tag attached to an outer face of the element 12.

In general, each first communication unit 14 comprises at least one antenna, a memory and, optionally, a microprocessor.

The antenna of each first communication unit 14 is, for example, a radiofrequency antenna.

The memory of each first communication unit 14 comprises information relating to the corresponding element 12.

Such information is, for example: a unique identifier of the element 12, the date of storage of the element 12, the expiry date of the element 12, the date on which the first communication unit 14 of the element 12 last provided information, the donation number relating to the content of the element 12, the product code of the content of the element 12, the rhesus group of the content of the element 12, the blood phenotype of the content of the element 12, the identity of the patient from which the content of the element 12 originates, the name of the patient from which the content of the element 12 originates, the volume of the content of the element 12, the donation center (including the address) where the content of element 12 was obtained, the current process on the element 12, and the type of anticoagulant of the content of the element 12. In the case of chemotherapy, such information includes, in addition, the date of manufacture, the type of product, the type of vehicle, the identity of the prescribing physician, the identity of the pharmacist, the identity of the manufacturer, the date of release and the state (released, issued, etc.).

The installation 10 comprises an enclosure 20 and a storage device 22.

The enclosure 20 includes an internal compartment 24 for receiving the storage device 22.

The enclosure 20 is, for example, a cooling enclosure, such as a refrigerator or a freezer. When the cooling enclosure is a refrigerator, the temperature of the enclosure is between 0 degrees Celsius (° C.) and 5°, preferably equal to 4° C. When the cooling enclosure is a freezer, the temperature of the enclosure is between −35° C. and −196° C., preferably equal to −40° C.

Alternatively, the enclosure 20 may be a platelet stirrer. The enclosure 20 is then preferably integrated in an incubator having a temperature, preferably equal to 24° C.

In what follows, relative positions are defined with respect to a current direction of use of the enclosure 20 for which a bottom is defined that generally rests on the floor and there is a top opposite the bottom. These relative positions are highlighted by terms such as "below" or "above".

The device 22 comprises a plurality of drawer assemblies 30 and a base 32. As shown in FIG. 2, the device 22 further comprises a processing unit 33.

Figure 3:
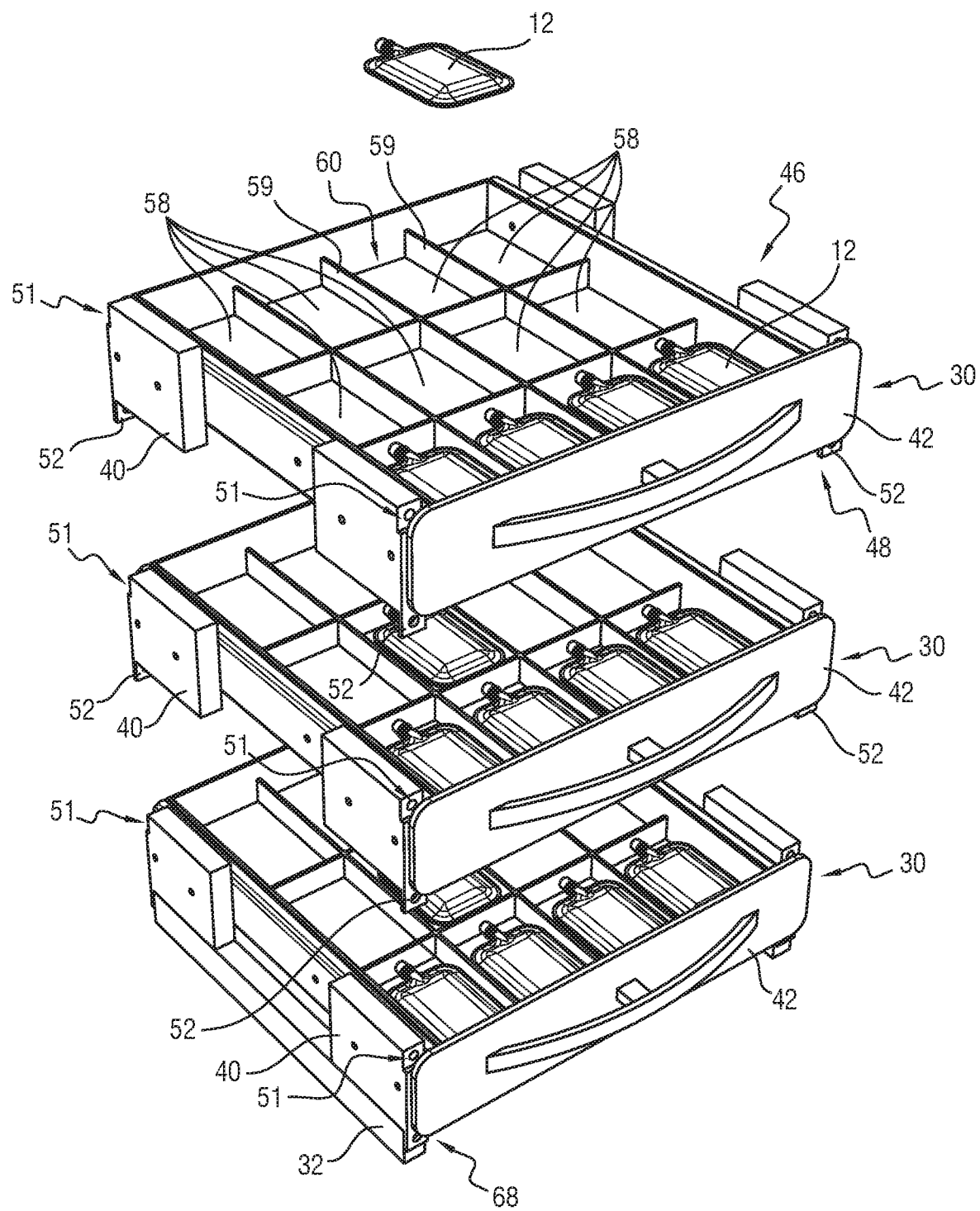
FIG. 3 shows a schematic representation of several drawer assemblies of the storage device of FIG. 1.

As described later, the drawer assemblies 30 are stacked on top of one another to form a vertical stack 38 of drawer assemblies 30. FIGS. 1 to 3 show an example of a stack of ten drawer assemblies 30.

Each drawer assembly 30 comprises a support 40, a drawer 42 and at least a second communication unit 44, visible in FIG. 2.

The support 40 comprises a housing 45, an upper end 46, a lower end 48 (visible in FIG. 3) and connections 49 (visible in FIG. 2). Optionally, each drawer assembly 30 also comprises a plate.

Each housing 45 is designed to receive the corresponding drawer 42.

The upper end 46 of each drawer assembly 30, visible in FIG. 3, and comprises at least a first assembly member 51. The first assembly members 51 are, for example, female connecting members.

The lower end 48 of each drawer assembly 30, visible in FIG. 3, comprises at least one second assembly member 52 that is complementary to the first assembly members 51. The second assembly members 52 are, for example, male assembly members.

In the example illustrated in FIG. 3, the first connecting members 51 are slots, while the second connecting members 52 are ribs that are complementary to the slots.

Thus, each drawer assembly 30 is assembled with at least one other drawer assembly 30 of the stack 38 by the first assembly member(s) 51 of the drawer assembly 30 and/or by the second one or two assembly member(s) 52 of the drawer assembly 30.

The connections 49 are, for example, electrical connections.

In the embodiment illustrated in FIGS. 1 to 3, the connections 49 of each drawer assembly 30 are connected, on the one hand, to the second communication units 44 of the drawer assembly 30, and, on the other hand, to the second communication units of the other drawer assemblies 30. In addition, the connections 49 are connected to the processing unit 33.

Each drawer 42 is positioned in the housing 45 of the support 40. Each drawer 42 is able to slide relative to the corresponding support 40.

Each drawer 42 comprises a bottom 56 defining at least one slot 58 to receive an element 12.

The bottom 56 of each drawer 42 consists of a material that may be traversed by radio waves emitted by the second communication unit 44 of the drawer assembly 30 of the drawer 42.

The material of the bottom 56 of each drawer 42 is, for example, plastic.

In the embodiment illustrated in FIGS. 1 to 3, the bottom 56 of each drawer 42 defines twelve slots 58 for receiving elements 12.

Each slot 58 is, for example, delimited by edges 59 to form a box 60.

In the embodiment illustrated in FIGS. 1 to 3, each drawer assembly 30 comprises as many second communication units 44 as there are slots 58.

Each second communication unit 44 is arranged below the bottom 56 of the drawer 42 in relation to the corresponding slot 58, in order to allow communication between the second communication unit 44 and the first communication unit 14 of an element 12 received in the slot 58. The expression "opposite" is understood to mean that each second communication unit 44 is arranged opposite the space delimited by the slot 58. In other words, the projection of the slot 58 in the plane of the second communication unit 44 is merged with the second communication unit 44.

Each second communication unit 44 is able to communicate, if necessary, with the first communication unit 14 of the element 12 received in the slot 58, in order to obtain information relating to the element 12.

Each second communication unit 44 is able to emit radio frequency waves. Each second communication unit 44 is designed to communicate with all the first communication units 14.

In an exemplary embodiment, the first communication units 14 are RFID tags, while the second communication units 44 are RFID readers.

More generally, each second communication unit 44 comprises at least one antenna, a memory, and, optionally, a microprocessor.

In the embodiment illustrated in FIGS. 1 to 3, each second communication unit 44 is integral with the drawer 42 of the corresponding drawer assembly 30. More specifically, each second communication unit 44 is fixed below the bottom 56 of the drawer 42 of the corresponding slot 58.

Alternatively, each second communication unit 44 is integral with the support 40 of the corresponding drawer assembly 30. Each drawer assembly 30 further includes a satellite. The satellite is a housing which contains the second communication unit 44. The satellite is fixed to the support 40 of the drawer assembly 30 directly under the drawer 42 of the drawer assembly 30. When the drawer 42 is closed, the second communication unit 44 is in a position facing the corresponding slot 58 and is therefore, if necessary, able to communicate with a first communication unit 14 positioned in the corresponding slot 58. When the drawer 42 is opened, the second communication unit 44 does not move with the drawer 42, and therefore is not able to communicate with a first communication unit 14 positioned in the corresponding slot 58.

Each plate is designed to prevent the passage of radio waves emitted by any second communication unit 44.

Each plate is positioned below the bottom 56 of the drawer 42 of each drawer assembly 30 and below the second communication units 44 corresponding to the slots 58 of the bottom 56 of the drawer 42 of the drawer assembly 30. Thus, each second communication unit 44 is only able to communicate with the first communication units 14 positioned above the second communication unit 44.

Each plate is, for example, made of metal.

The base 32 is assembled with the lowest drawer assembly 30 of the stack 38 of drawer assemblies 30. For this purpose, the base 32 comprises an upper end comprising at least a third assembly member 68. Each third assembly member 68 is identical to the first assembly member 51. The second assembly member(s) 52 of the last drawer assembly 30 of the stack 38 is/are assembled with the third assembly member(s) 68 of the base 32, which makes it possible to close the stack 38.

The processing unit 33 is able to process the information coming from the second communication units 44. In particular, the processing unit 33 is able to determine the occupation of each slot 58 and, where appropriate from the available information, the state of the element 12 positioned in the slot 58.

The states determined are, for example, two in number: a "valid" state and an "invalid" state. An element 12 is considered "valid" when the information relating to the element 12 conforms to a specification, or is otherwise considered "invalid".

Thus, the processing unit 33 has an instantaneous image of the storage device 22, namely which element 12 is in which slot 58 and the information relating to each of the elements 12. The processing unit 33 also comprises an input and output dates of each element 12 relative to the device 22.

In addition, the processing unit 33 is able to coordinate the second communication units 44. In particular, the processing unit 33 is able to activate each second communication unit 44 and to order, if necessary, the updating by the second communication unit 44 of the information contained in the first communication units 14.

Optionally, the processing unit 33 is able to trigger an alarm according to the occupation of each slot 58 and, if applicable, the state of the element 12 corresponding to the slot 58. For example, if the processing unit 33 determines that the same slot 58 comprises more than one element 12, the processing unit 33 triggers an alarm.

The operation of the device 22 integrated in the installation 10 will now be described.

When an element 12 is positioned in the slot 58 of one of the drawer assemblies 30 of the device 22, the second communication unit 44 corresponding to the slot 58, communicates with the first communication unit 14 of the element 12 in order to obtain information relating to the element 12. From the collected information, the processing unit 33 determines the state of each element 12, and, if necessary, either triggers an alarm or not.

Thus, the device 22 reliably controls the state of the elements 12 stored in the device 22, as well as the occupancy rate of the slots 58 of the drawer assemblies 30.

In addition, the specific positioning of the readers below the corresponding drawer offers a reduced footprint.

The device 22 is therefore an element storage device for reliably controlling the state of the elements 12 without encumbering the storage space.

In addition, it is easy to assemble and disassemble the drawer assemblies 30 of the device 22. Such modularity of the device 22 allows the device 22 to be adapted to suit a large number of installations 10 by modifying the number of drawer assemblies 30 in the stack 38.

In addition, a stack of drawer assemblies is much less heavy and cumbersome than a plurality of drawers, and is thus easier to handle and install.

In addition, from a manufacturing point of view, thousands of identical drawer assemblies are manufactured, rather than dozens of differently sized cabinets. This allows simplified stock management, and maintenance for economies of scale.

Furthermore, the device 22 may be adapted for an installation 10 that does not previously have RFID technology.

In addition, the reduced size makes it possible to envisage configurations in which the installation 10 contains a larger number of elements 12.

In addition, the installation 10 and/or the device 22 is/are easy to manufacture.

Finally, in the variant in which each drawer assembly 30 comprises a satellite, the satellite is in one assembly and is therefore easy to replace in the event of malfunction.

The invention claimed is:

1. A device configured to store a plurality of elements, each element including a wireless communication device, the device comprising:
    a plurality of drawer assemblies, each drawer assembly comprising
        an upper end and a lower end,
        a support comprising a housing and an assembly member with a respective complementary assembly member of the lower end or the upper end of the support of another of the drawer assemblies, so that the drawer assemblies are configured to be assembled on each other to form a vertical stack, a drawer positioned in the housing of the support and slidable relative to the support, the drawer comprising a bottom defining a plurality of slots configured to receive an element, for each slot, a single transmitter dedicated to the slot and configured to transmit radio frequency waves, the single transmitter being configured to communicate with all of the wireless communication devices, wherein the bottom of the drawer is made of a material configured to be traversed by radiofrequency waves emitted by the or each single transmitter, and wherein the or each single transmitter is disposed under the bottom of the drawer facing the corresponding slot of the bottom of the drawer in order to allow communication between the single transmitter and the wireless communication device of one of the elements received in the slot.

2. The device according to claim 1, wherein the bottom of the drawer is made of plastic.

3. The device according to claim 1, wherein the elements are containers of biological products, drugs or therapeutic preparations.

4. The device according to claim 1, wherein each wireless communication device is a radio identification tag, and each single transmitter is a radio identification reader.

5. The device according to claim 1, wherein each single transmitter is secured to the support of the corresponding drawer assembly.

6. The device according to claim 1, wherein each single transmitter is secured to the drawer of the corresponding drawer assembly.

7. The device according to claim 1, wherein each wireless communication device comprises information relative to the respective element, wherein each single transmitter is, when it is appropriate, configured to communicate with the wireless communication device of the element received in the slot opposite the single transmitter to obtain information relative to the element when it is appropriate for the respective single transmitter to communicate with the wireless communication device, the device further comprising a processor connected to each single transmitter, the processor being configured to determine, from the communicated information, an occupation of each slot and, when it is appropriate, a state of the element received in the slot, the processor being configured to trigger an alarm according to the occupation of each slot and, when it is appropriate, the state of the element corresponding to the slot.

8. An installation comprising:

an enclosure comprising an internal compartment; and the device according to claim 1, the device being disposed in the internal compartment of the enclosure.

9. The installation according to claim 8, wherein the enclosure is a refrigerating enclosure.

10. The installation according to claim 8, wherein the elements are platelet containers, and the enclosure is a platelet stirrer.

11. A device configured to store a plurality of elements, each element including a wireless communication device, the device comprising:

a plurality of drawer assemblies, each drawer assembly comprising a support comprising a housing, a drawer positioned in the housing of the support and slidable relative to the support, the drawer comprising a bottom defining a plurality of slots configured to receive an element, for each slot, at least one transmitter dedicated to the slot and configured to transmit radio frequency waves, the at least one transmitter being configured to communicate with all of the wireless communication devices, wherein the bottom of the drawer is made of a material configured to be traversed by radiofrequency waves emitted by the or each transmitter, wherein the or each transmitter is disposed under the bottom of the drawer facing the corresponding slot of the bottom of the drawer in order to allow communication between the at least one transmitter and the wireless communication device of one of the elements received in the slot, and wherein each transmitter is secured to the drawer of the corresponding drawer assembly.

* * * * *